United States Patent
McLawhorn et al.

(10) Patent No.: US 9,888,960 B2
(45) Date of Patent: Feb. 13, 2018

(54) HANDLE AND POWER CORD ASSEMBLIES FOR BIPOLAR ELECTROSURGICAL DEVICES

(71) Applicant: Cook Medical Technologies LLC, Bloomington, IN (US)

(72) Inventors: Tyler McLawhorn, Winston-Salem, NC (US); John Crowder Sigmon, Jr., Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 602 days.

(21) Appl. No.: 14/534,973

(22) Filed: Nov. 6, 2014

(65) Prior Publication Data

US 2015/0133924 A1 May 14, 2015

Related U.S. Application Data

(60) Provisional application No. 61/901,724, filed on Nov. 8, 2013.

(51) Int. Cl.
 *A61B 18/14* (2006.01)
 *A61B 18/00* (2006.01)
 (Continued)

(52) U.S. Cl.
 CPC ...... *A61B 18/1482* (2013.01); *A61B 18/1492* (2013.01); *A61B 2017/0042* (2013.01);
 (Continued)

(58) Field of Classification Search
 CPC .................. A61B 18/1482; A61B 2018/00946
 See application file for complete search history.

(56) References Cited

U.S. PATENT DOCUMENTS 3,699,968 A  10/1972  Bolduc
4,112,941 A   9/1978  Larimore
(Continued)

FOREIGN PATENT DOCUMENTS

EP  0 440 385 A2   8/1991
EP  0 572 131 A1  12/1993
(Continued)

OTHER PUBLICATIONS

Invitation to Pay Additional Fees and Annex to Form PCT/ISA/206, Communication Relating to the Results of the Partial International Search for corresponding PCT Application PCT/US2014/064294 dated Feb. 27, 2015.
(Continued)

*Primary Examiner* — William Levicky

(57) ABSTRACT

Bipolar electrosurgical devices may include a handle assembly configured to control movement of components of the electrosurgical device to perform an electrosurgical procedure and a power cord assembly configured to electrically connect the bipolar electrosurgical device with a power source. For bipolar sphincterotomes, an active portion of the handle assembly may include a first active member that contacts and slides across a second active member as the gripping portion moves about a handle stem component of the handle assembly. The power cord assembly may include a pair of return contacts that are shorted together when connected with the handle assembly, which in turn may deactivate an alarm output by the power source.

22 Claims, 7 Drawing Sheets

(51) Int. Cl.
*A61B 17/00* (2006.01)
*H01R 11/30* (2006.01)

(52) U.S. Cl.
CPC ............ *A61B 2017/00424* (2013.01); *A61B 2018/0091* (2013.01); *A61B 2018/00178* (2013.01); *A61B 2018/00553* (2013.01); *A61B 2018/00601* (2013.01); *A61B 2018/00898* (2013.01); *A61B 2018/00946* (2013.01); *A61B 2018/144* (2013.01); *H01R 11/30* (2013.01); *H01R 2201/12* (2013.01)

(56) References Cited

U.S. PATENT DOCUMENTS

| | | | |
|---|---|---|---|
| 4,211,456 A | | 7/1980 | Sears |
| 5,026,371 A | | 6/1991 | Rydell et al. |
| 5,035,696 A | * | 7/1991 | Rydell .............. A61B 18/14 606/47 |
| 5,201,732 A | | 4/1993 | Parins et al. |
| 5,810,807 A | | 9/1998 | Ganz et al. |
| 5,813,996 A | | 9/1998 | St. Germain et al. |
| 6,311,692 B1 | * | 11/2001 | Vaska ............... A61B 18/1402 606/41 |
| 7,121,827 B2 | | 10/2006 | Lampert |
| 7,182,604 B2 | | 2/2007 | Ehr et al. |
| 7,442,042 B1 | | 10/2008 | Lewis |
| 7,722,412 B2 | | 5/2010 | Ehr et al. |
| 7,935,130 B2 | | 5/2011 | Williams |
| 7,963,773 B2 | | 6/2011 | Palli et al. |
| 2003/0216723 A1 | | 11/2003 | Shinmura et al. |
| 2008/0311765 A1 | | 12/2008 | Chatterjee et al. |
| 2011/0087217 A1 | | 4/2011 | Yates et al. |
| 2012/0100729 A1 | | 4/2012 | Edidin et al. |

FOREIGN PATENT DOCUMENTS

| | | |
|---|---|---|
| JP | H06-30947 A | 2/1994 |
| JP | H07-51288 A | 2/1995 |

OTHER PUBLICATIONS

International Search Report and Written Opinion for corresponding PCT Application PCT/US2014/064294 dated Jul. 10, 2015.

\* cited by examiner

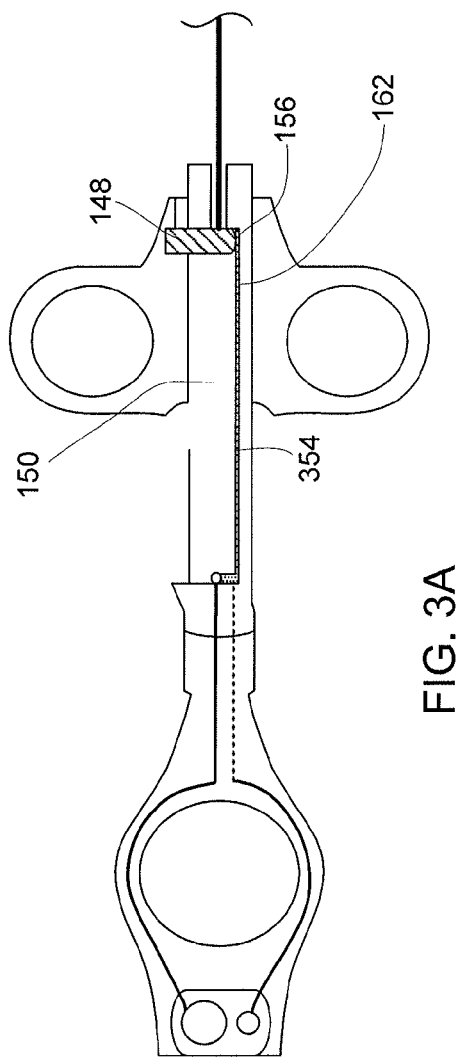
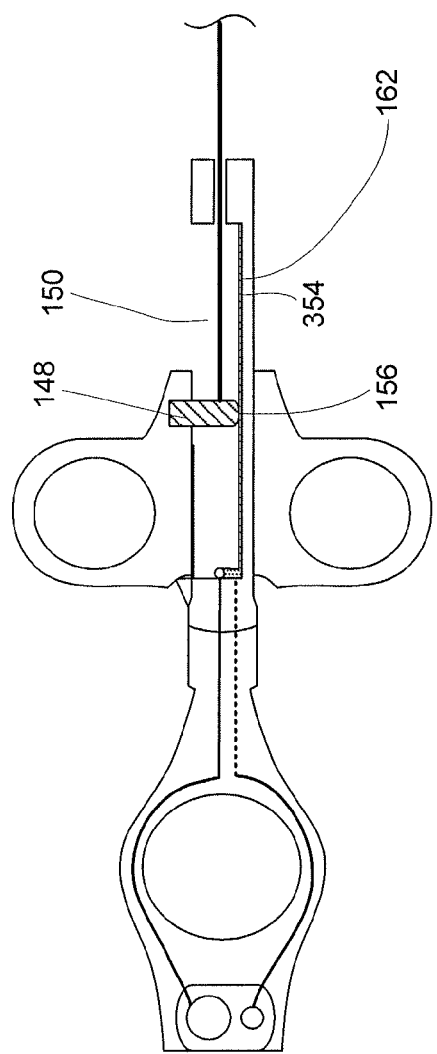
FIG. 3A
FIG. 3B

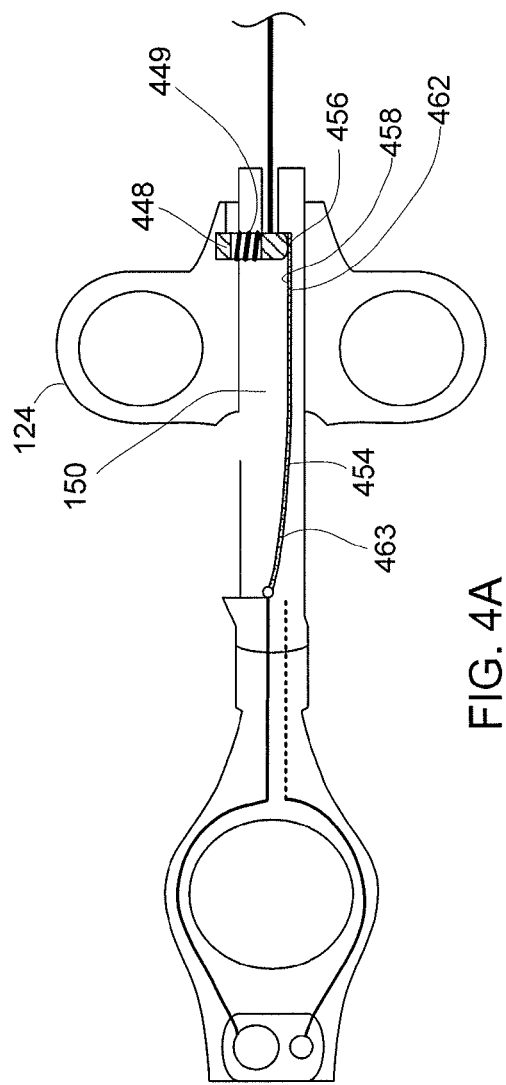
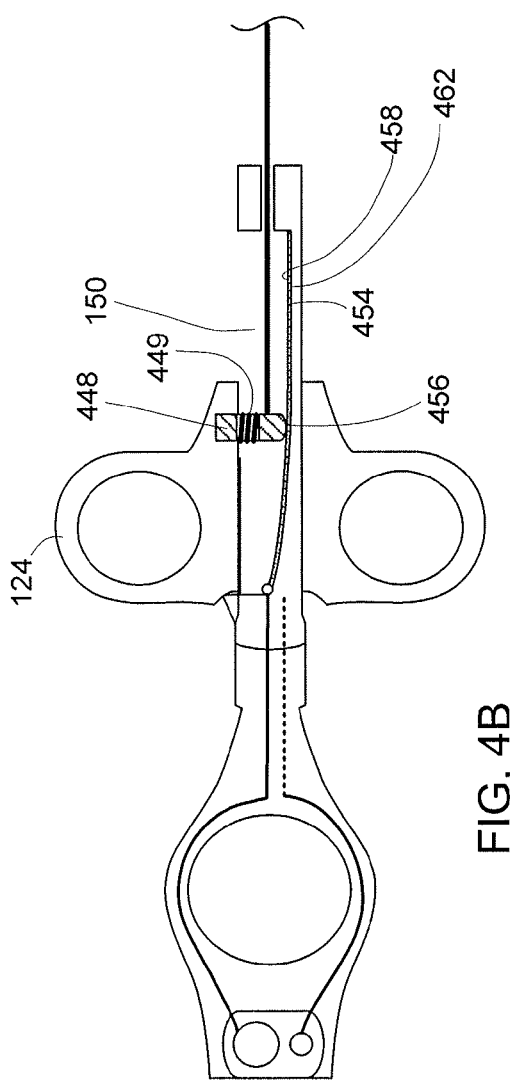
FIG. 4A
FIG. 4B

HANDLE AND POWER CORD ASSEMBLIES FOR BIPOLAR ELECTROSURGICAL DEVICES

CROSS REFERENCE TO RELATED APPLICATION

This application claims the benefit of U.S. Provisional Application No. 61/901,724, filed Nov. 8, 2013. The contents of U.S. Provisional Application No. 61/901,724 are incorporated by reference in their entirety.

TECHNICAL FIELD

The present invention relates generally to medical devices, and more particularly to bipolar sphincterotomes.

BACKGROUND

A sphincterotome is a medical device that is used to perform a sphincterotomy, which involves cutting a sphincter muscle, such as the sphincter of Oddi. The sphincter muscle may need to be cut to relieve its constrictive nature and allow one or more medical devices through the muscle. For example, problems occurring in the biliary tree, such as the formation of bile duct stones or papillary stenosis, may be treated using medical devices that are delivered into the biliary tree. In order to access the biliary tree, the medical devices may pass through the sphincter of Oddi. To facilitate passage of the medical devices through the sphincter of Oddi, the sphincter muscle may be cut using a sphincterotome.

A sphincterotome may generally include an elongate tubular member, such as a catheter, and a cutting wire that is used to cut the sphincter muscle. The cutting wire may extend through a lumen of the catheter, except at a distal portion of the catheter, where the cutting wire may project from and be exposed outside of the catheter. The exposed portion, which may be referred to as a cutting edge, may be used to cut the sphincter muscle.

A sphincterotomy generally involves a two-part process: cannulation of the biliary tree and cutting the sphincter muscle by sending electric current through the cutting wire (i.e, electrosurgery). Cannulation of the biliary tree may include inserting the distal portion of the catheter into the papilla and using the distal portion and the cutting edge to lift an upper portion (i.e., the roof) of the papilla. The roof of the papilla may be lifted by proximally pulling the cutting wire taut, causing the distal portion of the tubular member to bow and form an arc. After cannulation, the electric current may be provided to the cutting edge to cut the sphincter muscle.

BRIEF SUMMARY

In a first aspect, a bipolar electrosurgical device may include an elongate tubular member; an active path configured to deliver electrical current generated by a power source to a treatment site, where the active path includes an active wire movably disposed and longitudinally extending in the tubular member; a return path configured to return the electrical current to the power source; and a handle assembly. The handle assembly may include an elongate handle stem portion comprising a body and a channel longitudinally extending in the body; and a gripping portion movably disposed about the handle stem portion and operably coupled to a proximal end of the active wire. The return path may include a return member disposed in the handle stem portion. Also, the gripping portion may be configured to move the proximal end of the cutting wire in the channel relative to the return member.

In a second aspect, a handle assembly for a bipolar electrosurgical device may include an elongate handle stem portion that includes a body and a channel longitudinally extending in the body; a return portion of a return path of the bipolar electrosurgical device, where the return portion includes a return member disposed in the handle stem portion; a gripping portion movably disposed about the handle stem portion; and an active portion of an active path of the bipolar electrosurgical device. The active portion may include a first active member fixedly attached to the gripping portion. The first active member may be configured to be coupled to a proximal end of an active wire. In addition, the first active member may be configured to move the proximal end of the active wire in the channel relative to the return path portion.

In a third aspect, a bipolar electrosurgical device configured to perform an electrosurgical procedure at a treatment site within a patient may include: an elongate tubular member; an active path and a return path having a bipolar configuration with the elongate tubular member, where the active path may be configured to supply electrical current generated by a power source to the treatment site, and the return path may be configured to return the electrical current back to the power source; a handle assembly; and a power cord assembly. The handle assembly may include a first active contact electrically coupled to the active path; and a first return contact electrically coupled to the return path. The power cord assembly may be configured for removable attachment with the handle assembly and include a second active contact, a second return contact, and a third return contact. The second active contact, the second return contact, and the third return contact may be sufficiently electrically isolated from each other when disconnected from the first active contact and the first return contact of the handle assembly. In addition, the second return contact and the third return contact may be shorted together by the first return contact when connected to the first return contact.

In a fourth aspect, a power cord assembly for a bipolar electrosurgical device may be configured to conduct electrical current between a power source and the bipolar electrosurgical device and include: a mating connector configured for removable attachment with a corresponding mating area of a handle assembly of the bipolar electrosurgical device; and a plurality of contacts disposed on the mating connector and configured for electrical contact with a first active contact and a first return contact of the handle assembly. The first active contact may be part of an active path for the bipolar electrosurgical device. The first return contact may be part of a return path for the bipolar electrosurgical device. The plurality of contacts may include a second active contact, a second return contact, and a third return contact. Additionally, the plurality of contacts may be sufficiently electrically isolated from each other when the mating connector is detached from the mating area of the handle assembly. Further, the second and third return contacts may be in contact with and shorted together by the first return contact and the second active contact may be in contact with the first active contact when the mating connector is attached to the mating area of the handle assembly.

In a fifth aspect, a method of deactivating an alarm output by a power source, where the alarm indicates an insufficient connection between the power source and a bipolar electrosurgical device, may include: electrically connecting a first return contact disposed on a handle assembly for the bipolar electrosurgical device with a second return contact of a power cord assembly; electrically connecting the first return contact disposed on the handle assembly with a third return contact of the power cord assembly, the second and third return contacts being shorted together when electrically connecting the first return contact with the second and third return contacts; and in response to the second and third active contacts being shorted together, deactivating the alarm being output by the power source.

BRIEF DESCRIPTION OF THE DRAWINGS

FIG. 3A shows a cross-sectional side view of an alternative configuration of the handle assembly of the bipolar sphincterotome shown in FIGS. 1A and 1B, with a gripping portion in a distal position.

FIG. 3B shows a cross-sectional side view of the alternative configuration of the handle assembly shown in FIG. 3A, with the gripping portion in the proximal position.

FIG. 4A shows a cross-sectional side view of a second alternative configuration of handle assembly of the bipolar sphincterotome shown in FIGS. 1A and 1B, with a gripping portion in a distal position.

FIG. 4B shows a cross-sectional side view of the second alternative configuration of the handle assembly shown in FIG. 4A, with the gripping portion in the proximal position.

DETAILED DESCRIPTION

The present disclosure describes handle assemblies and power cord assemblies for electrosurgical devices having a bipolar configuration, otherwise referred to as bipolar electrosurgical devices. An electrosurgical device may be any medical device configured to perform an electrosurgical procedure at a treatment site within a patient. To perform the electrosurgical procedure, the electrosurgical device may include an active path and a return path that are electrically coupled to a power source. The active path may longitudinally extend within an elongate tubular member, such as a catheter, of the electrosurgical device and may supply electrical current generated by the power source to the treatment site. The return path may return the supplied current back to the power source. The return path for bipolar electrosurgical devices may be attached to, adhered to, integrated with, disposed within, or included as part of the elongate tubular member. The return path for bipolar electrosurgical devices may differ from return paths for monopolar electrosurgical devices, which may use a neutral electrode (e.g., a solid, neutral electrode or a split neutral electrode) positioned on a thigh of the patient as part of the return path. The bipolar electrosurgical devices of the present disclosure may utilize and/or connect to power sources that are configured to recognize monopolar electrosurgical devices using neutral electrodes. Exemplary bipolar electrosurgical devices may include bipolar sphincterotomes, needle knives, snares, or forceps. Other bipolar electrosurgical devices, including bipolar endoscopic electrosurgical devices, may be possible.

Figure 1A:
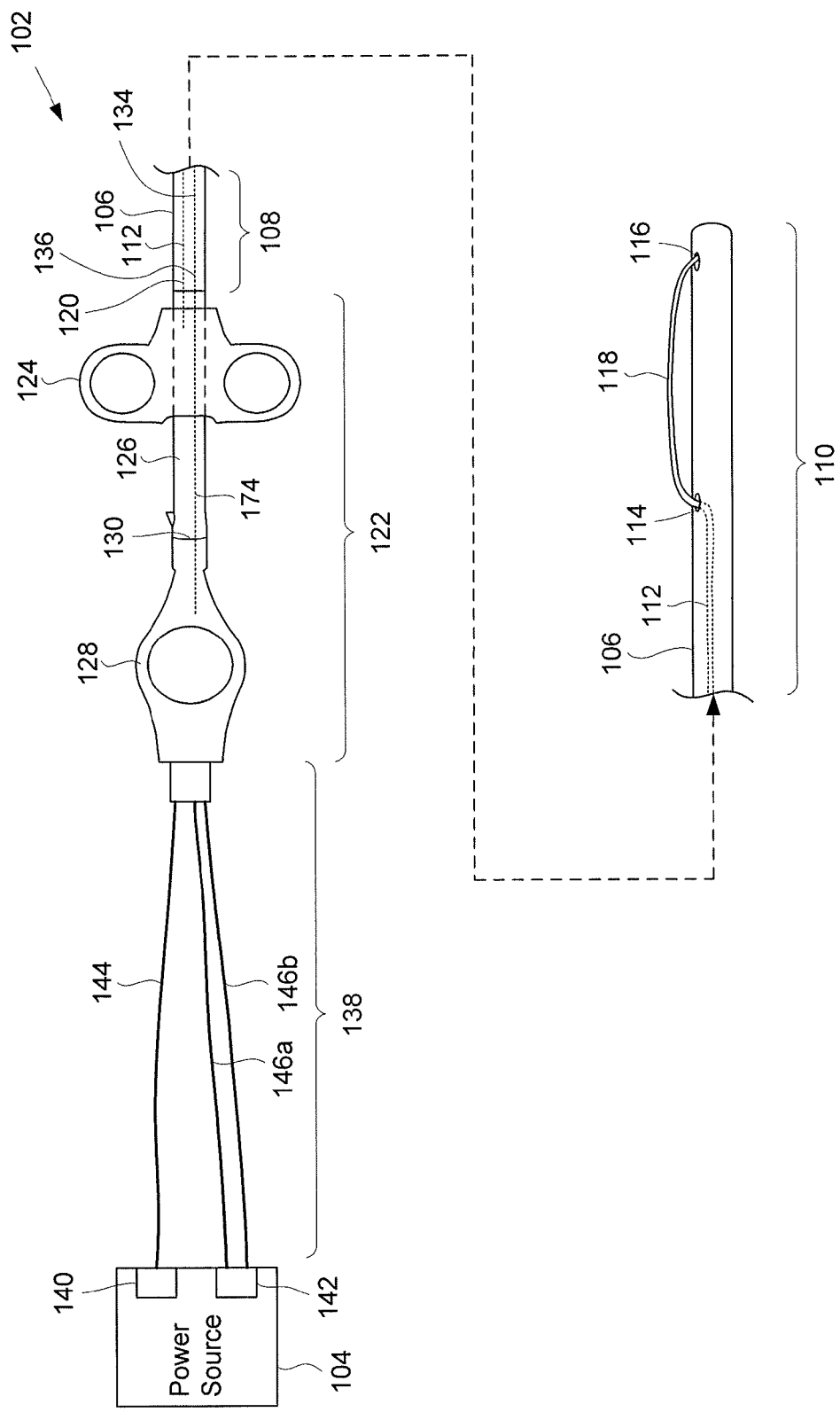
FIG. 1A shows a side view of a bipolar sphincterotome connected to a power source, with a cutting edge in a relaxed position.
Figure 1B:
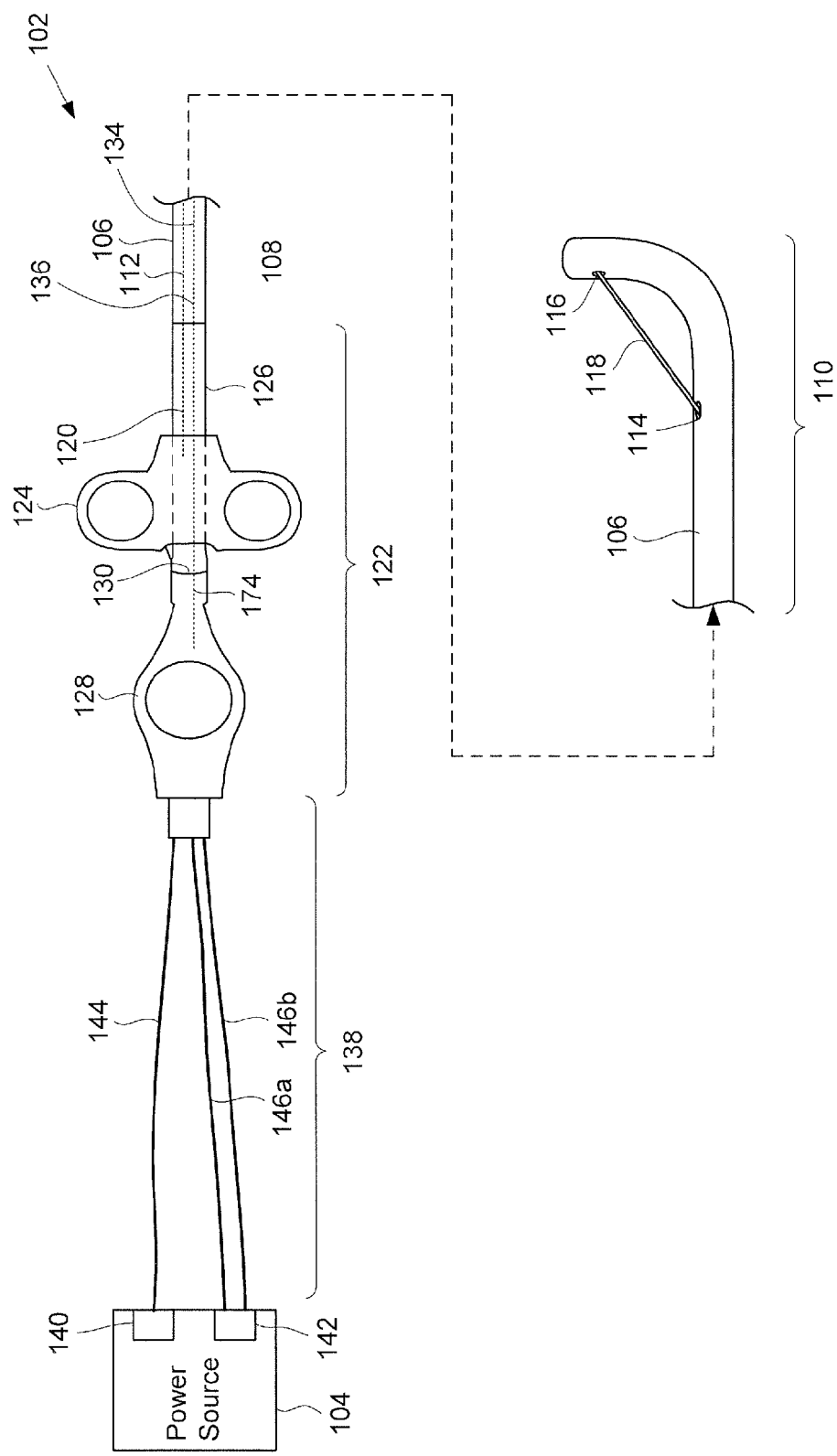
FIG. 1B shows a side view of the bipolar sphincterotome of FIG. 1A, with the cutting edge in a cutting position.

FIGS. 1A and 1B show side views of a bipolar sphincterotome 102 electrically connected to a power source 104. The bipolar sphincterotome 102 may include an elongate tubular member 106 that extends from a proximal portion 108 to a distal portion 110. A cutting or active wire 112 used to cut a sphincter muscle at a treatment site within a patient may be disposed within a lumen (not shown in FIG. 1) of the tubular member 106 from the proximal portion 108 to the distal portion 110. At the distal portion 110, the cutting wire 112 may extend or protrude from within the tubular member 106, through a first opening 114 of the tubular member 106, to outside the tubular member 106. Outside the tubular member 106, the cutting wire 112 may longitudinally extend substantially parallel with the tubular member 106 to a second opening or anchor point 116 that is distal the first opening 114, where a distal end of the cutting wire 112 may re-enter and/or be fixedly attached to the tubular member 106. The exposed portion 118 of the cutting wire 112 may be referred to as a cutting edge, which may be the portion of the cutting wire 108 that cuts the sphincter muscle.

The cutting edge 118 may move between a cutting position and a relaxed position. The cutting edge 118 may be positioned in the cutting position when a user of the sphincterotome 102 intends to lift the roof of the papilla and/or cut the sphincter muscle. The cutting edge 118 may be positioned in the relaxed position when the user intends to perform an action other than lifting the roof of the papilla or cut the sphincter muscle, such as delivering the distal portion 110 to and from the treatment site or cannulating the biliary tree, as examples. FIG. 1A shows the cutting edge 118 in the relaxed position. In the relaxed position, the cutting edge 118 may have relatively little tension. Additionally, the distal portion 110 of the tubular member 106 may be configured in a generally straight position. The cutting edge 118 may be moved from the relaxed position to the cutting position by proximally pulling the cutting wire 112 taut, which in turn may cause the distal portion 110 of the tubular member 106 to bow or curl and form an arc. FIG. 1B shows the distal portion 110 in a curled position with the cutting wire 112 taut and the cutting edge 118 in the cutting position. Geometrically, when the distal portion 110 is in the curled position, the distal portion 110 may form an arc and the cutting edge 118 may form a secant of the arc.

A proximal end 120 of the cutting wire 112 may be operably connected to a handle assembly 122 that is configured to move the cutting edge 118 between the relaxed and cutting positions. In particular, the handle assembly 122 may include a first gripping portion 124 operably connected to the cutting wire 112. The first gripping portion 124 may be movably disposed about an elongate handle stem portion 126 and configured to longitudinally move relative to the handle stem portion 126 between a proximal position and a distal position. FIG. 1A shows the first gripping portion 124 in the distal position. FIG. 1B shows the first gripping portion 124 in the proximal position. When the first gripping portion 124 is in the distal position, the cutting edge 118 may be in the relaxed position. Proximally moving the first gripping portion 124 from the distal position to the proximal position may proximally pull the wire 112 taut and move the cutting edge 118 from the relaxed position to the cutting position, as shown in FIG. 1B. Vice versa, distally moving the first gripping portion 124 from the proximal position to the distal position may distally advance the cutting wire 112 and move the cutting edge 118 from the cutting position to the relaxed position, as shown in FIG. 1A.

The handle assembly 122 may also include a second gripping portion 128. The second gripping portion 128 may be positioned proximal the first gripping portion 124, and may be gripped by a user of the sphincterotome 102 to assist the user in moving the first gripping portion 124 between the proximal and distal positions. In some example embodiments, as shown in FIGS. 1A and 1B, the first and second gripping portions 124, 128 may be ringed-shaped structures configured to receive one or more fingers or a thumb of the user. For example, the first gripping portion 124 may be a dual-ringed structure configured to receive two fingers, such as the middle finger and the ring finger, of the user. The second gripping portion 128 may be a single-ringed structure configured to receive a thumb of the user. Other ringed-shaped structure or structures other than ringed-shaped configured for gripping by the user may alternatively be used. The second gripping portion 128 may be fixedly connected to a proximal end 130 of the handle stem portion 126. The first gripping portion 124 may move relatively to both the handle stem portion 126 and the second gripping portion 128 between the proximal and distal positions to move the cutting edge 118 between the cutting and relaxed positions.

The cutting wire 112 may be part of an active electrical path that is configured to conduct and deliver electrical current to the cutting edge 118 to cut the sphincter muscle at the treatment site. To conduct and deliver the current, the cutting wire 112 may be electrically coupled to the power source 104. The power source 104 may be configured to generate and/or supply electrical current to the cutting wire 112. Examples of the power source 104 may be a radio frequency (RF) generator or an electrosurgical unit (ESU). The electrical current that is supplied may be returned back to the power source 104 using a return path. By being a bipolar sphincterotome 102, a return wire 134 of the return path may be attached to, integrated with, disposed within, or included as part of the tubular member 106. FIGS. 1A and 1B show a proximal end 136 of the return wire 134 extending within a proximal portion 108 of the tubular member 106. Although not shown in FIGS. 1A and 1B, the return wire 134 may distally extend to the distal portion 110 of the tubular member 106, where the return wire 134 may be electrically connected to a return electrode integrated or implemented with the distal portion 110 of the tubular member. Various configurations or implementations of the distal end of the return wire and the return electrode for the bipolar configuration may be possible, and is considered outside the scope of the present description.

As described in further detail below, the cutting and return wires 112, 134 may each be electrically coupled to respective active and return portions embedded or integrated with the handle assembly 122. The active and return portions of the handle assembly 122 may, in turn, be electrically connected to active and return portions of a power cord assembly 138, which may be configured to electrically and physically connect to active and return ports 140, 142 of the power source 104. As shown in FIGS. 1A and 1B, the power cord assembly 138 may include three wires or other conductive paths, including an active wire 144 and a pair of return wires 146a, 146b electrically insulated from each other. The active wire 144 may be configured to connect to the active port 140 of the power source 104. The return wires 146a, 146b may be configured to connect to the return port 142 of the power source 104.

The three-wire configuration of the power cord assembly 138 may be adapted to operate with power sources, such as ESUs, configured to connect with and recognize monopolar sphincterotomes that use a split neutral electrode. When the power source 104 is set to recognize a monopolar sphincterotome that uses a split neutral electrode, the power source 104 may output an alarm or other indication of an electrical disconnection between the power source 104 and the bipolar sphincterotome 102 unless the power cord assembly 138 is sufficiently electrically connected to both the power source 104 and the handle assembly 122, as described in further detail below.

Figure 2C:
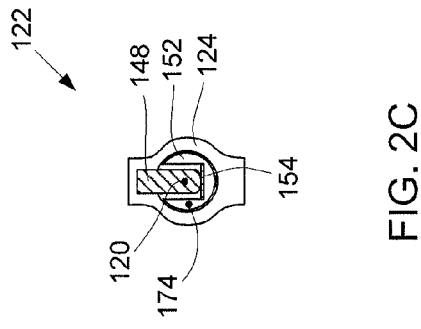
FIG. 2C shows a cross-sectional axial view of the configuration of the handle assembly shown in FIG. 2A taken along line 2C-2C.
Figure 2A:
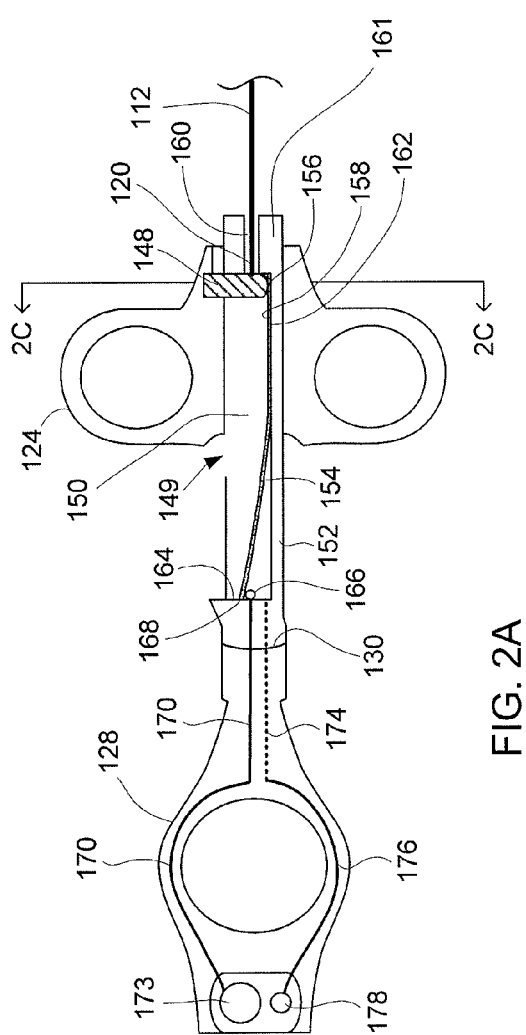
FIG. 2A shows a cross-sectional side view of a configuration of a handle assembly of the bipolar sphincterotome shown in FIGS. 1A and 1B, with a gripping portion in the distal position.
Figure 2B:
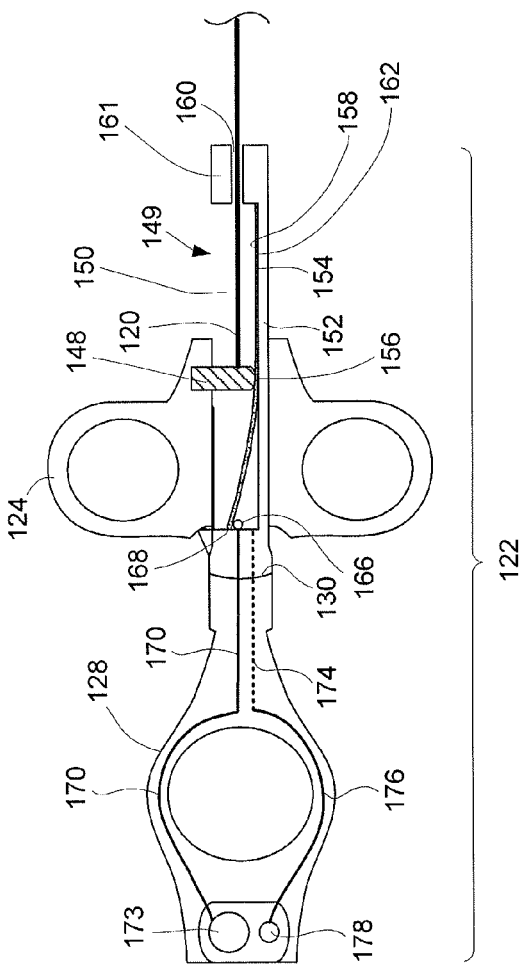
FIG. 2B shows a cross-sectional side view of a configuration of the handle assembly of the bipolar sphincterotome shown in FIGS. 1A and 1B, with the gripping portion in the proximal position.

FIGS. 2A and 2B show cross-sectional side views of the handle assembly 122 disconnected from the power cord assembly 138 and connected to the proximal end 120 of the cutting wire 112. FIG. 2C shows a cross-sectional axial view of the handle assembly 122 taken along line 2C-2C in FIG. 2A. FIG. 2A shows the first gripping portion 124 in the distal position. FIG. 2B shows the first gripping portion 124 in the proximal position.

The active portion of the active path that is included or integrated with the handle assembly 122 may include a conductive first active member 148 fixedly attached to the first gripping portion 124. The first active member 148 may extend from the first gripping portion 124 through an opening 149 into a hollow channel 150 of the handle stem portion 126. The channel 150 may longitudinally extend in a stem body 152 of the handle stem portion 126 and be defined by an inner surface of the stem body 152. The first active member 148 may also be electrically connected as well as securely and/or fixedly attached to the proximal end 120 of the cutting wire 112. A hole or opening 160 may longitudinally extend in a distal end 161 of the stem body 152, through which the cutting wire 112 may be disposed. When the first gripping portion is longitudinally moved about the handle stem portion 126, the first active member 148 and the proximal end 120 of the cutting wire 112 may, in turn, longitudinally move within the channel 150 of the handle stem portion 126.

The active portion of the active path included or integrated with the handle assembly 122 may also include a conductive second active member 154 disposed and longitudinally extending in the channel 150. The first active member 148 may extend in the channel 150 such that an end 156 of the first active member 148 contacts and forms an electrical connection with an outer surface 158 of the second active member 154. Because the first active member 148 is fixedly attached to the first gripping portion 124, the end 156 of the first active member 148 may move or slide across the outer surface 158 proximally and distally as the first gripping portion 124 proximally and distally moves about the handle stem portion 126 between the proximal and distal positions. In this way, as the first gripping portion 124 longitudinally moves about the handle stem portion 126, the first active member 148 and the proximal end 120 of the cutting wire 112 may longitudinally move relative to the second active member 154. As the end 156 of the first active member 148 slides across the outer surface 158 of the second active member 154, electrical contact may be maintained.

The end 156 of the conductive member 148 may be rounded to reduce or minimize friction between the end 156 and the top surface 158. In one example configuration, the conductive member may include a pin, such as a brass pin, integrated with a ball-like object, such as a copper ball as the rounded end 156. The proximal end 120 may extend in a side hole of the pin, and a screw may be inserted inside the pin to secure the proximal end 120 to the pin. Other configurations of the conductive member 148 may be possible.

For some example configurations, a distal portion of the second active member 154 may be disposed on a bottom inner surface portion 162 of the inner surface of the stem body 152. A proximal portion of the second active member 154 may proximally extend upward from the bottom inner surface portion 162 to a position along a proximal side inner surface portion 164 adjacent the bottom inner surface portion 162. The second active member 154 may be made of a flexible or other conductive material configured to elastically recoil, such as Nitinol, spring steel, copper, or gold as non-limiting examples. By proximally extending upward from the bottom inner surface portion 162, the proximal portion of the second active member 154 may be configured to flex downward due to a downward bias on the second active member 154 by the first active member 148 as the first gripping portion 124 is moved to the proximal position, as shown in FIG. 2B. The proximal portion of the second active member 154 may be configured to proximally extend upward to the proximal side inner surface portion 164 and flex in order to enhance the contact between the end 156 of the first active member 148 and the outer surface 158 of the second active member 154.

In alternative configurations, rather than be configured in the channel 150 to flex, the second active member 154 may be rigidly positioned in the channel 150 and/or the second active member 154 may not be configured to flex as the end 156 of the first active member 148 slides across the outer surface 158 of the second active member 156. For example, as shown in FIGS. 3A and 3B, both the proximal and distal portions of a conductive strip 354 may be disposed on the bottom inner surface portion 162. As another example, as shown in FIGS. 4A and 4B, a proximal end 463 of a bottom inner surface 462 may incline or ramp up and an alternative second active member 454 may extend along the bottom inner surface 462. An alternative first active member 448 may be configured with a spring 449 which may expand and contract as the first gripping portion 124 moves an end 456 of the first active member 448 along an outer surface 458 of the second active member 454. In general, the conductive strip may provide a track in the handle stem portion 126 over which the conductive member 148 may slide across and maintain an electrical connection.

Referring back to FIGS. 2A and 2B, a solder ball or other conductive material 166 may be positioned along the proximal side inner surface portion 164. A proximal end 168 of the conductive strip 154, which may also be positioned along the proximal side inner surface portion 164, may be electrically connected with the solder ball 166. The active portion of the active path included or integrated with the handle assembly 122 may further include a proximal conductive active path 170 that extends from the solder ball 166, through the proximal end 130 of the handle stem portion 126, through the ringed structure of the second gripping portion 128, to an active contact 173 positioned on the second gripping portion 128.

Referring to FIG. 2C, the return portion of the return path included or integrated with the handle assembly 122 may include a conductive return member 174 disposed or embedded in the stem body 152 adjacent the channel 150. For some example configurations, as shown in FIG. 2C, the return member 174 may be a wire longitudinally extending in the body, although configurations other than a wire may be possible. The stem body 152 may be made of an electrically insulating material, such as polycarbonate or plastic as examples, so that the return member 174 of the return path and the second active member 154 are electrically isolated from each other. The return member 174 embedded in the stem body 152 may be offset from the center axis, as shown in FIG. 2C, although various positions in the stem portion 126 may be possible. For example, the return member 174 may be positioned in the channel 150, alongside but electrically isolated from, first and second active members 148, 154. Additionally, the return member 174 may longitudinally extend in the stem portion 126 from the distal end 161 to the proximal end 130, and may proximally extend further to the second gripping portion 128, as shown in FIGS. 1A-2B. The return portion of the return path included or integrated with the handle assembly 122 may further include a proximal conductive return path 176 electrically connected with the wire 174 embedded in the handle stem portion 126 and extending to a return contact 178 positioned on the second gripping portion 128.

As shown FIG. 2C, the second active member 154 may be a relatively thin conductive strip, with the width second active member 154 being greater than its height. Alternatively, the second active member 154 may be made of other conductive materials and/or be other conductive structures, such as a wire, conductive ink, a conductive cannula, or an overmolded material.

The active and return portions included and/or integrated with the handle assembly may be configured to move relative to each other, which may correspond to the movement of the first gripping portion 124 relative to the handle stem portion 126. In particular, as the first gripping portion 124 longitudinally moves relative to the handle stem portion 126, the first active member 148 may longitudinally move relative to each of the second active member 154 and the return member 174.

Referring back to FIGS. 1A and 1B, the power source 104 may be configured to detect whether there is an incomplete or insufficient electrical connection between the active and return ports 140, 142 of the power source 104 and the active and return paths of the bipolar sphincterotome 102. When the power source 104 detects the incomplete or insufficient electrical connection, the power source 104 may output an alarm or other indication, including an audio and/or visual alarm or indication, indicating the incomplete or insufficient electrical connection. Alternatively, when the power source 104 detects a complete or sufficient electrical connection between the active and return ports 140, 142 and the active and return paths, the power source 104 may deactivate the alarm or indication.

Figure 5:
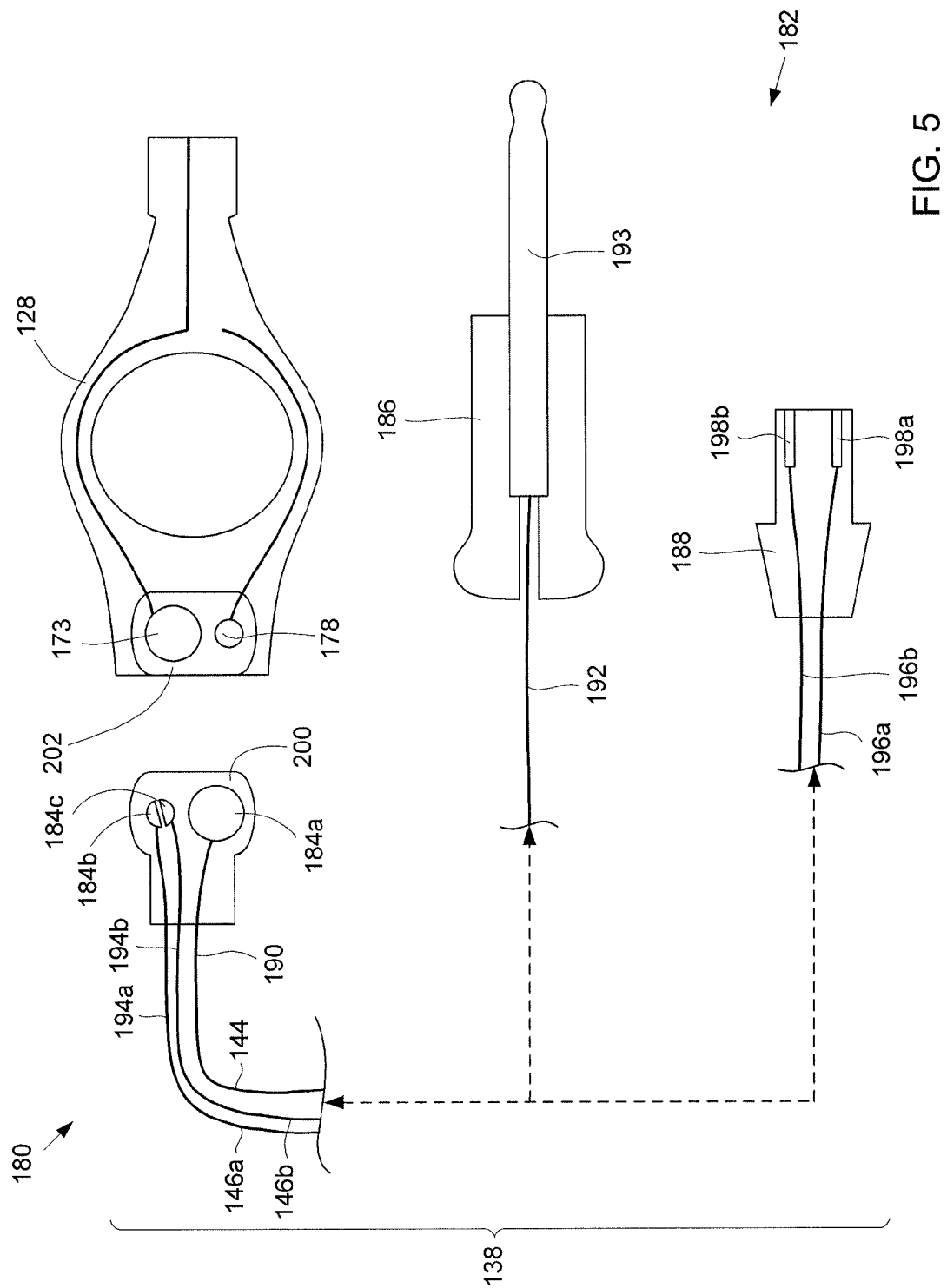
FIG. 5 shows a cross-sectional side view of a distal gripping portion of the handle assembly and first and second ends of a power cord assembly.

Referring to FIG. 5, a cross-sectional side view of the second gripping portion 128 in isolation from the rest of the handle assembly 122, and first and second ends 180, 182 of the power cord assembly 138 are shown. The first end 180 may include a plurality of contacts 184 configured for contact with the active contact 173 and the return contact 178 of the handle assembly 122. The second end 182 may include an active jack or connector 186 and a return plug or connector 188. The active connector 186 may be adapted for a removable connection with the active port 140 of the power supply 104 (FIGS. 1A, 1B). The return connector 188 may be adapted for a removable connection with the return port 142 of the power supply 104. When each of the active and return connectors 186, 188 are connected to the active and return ports 140, 142 respectively, the power cord assembly 138 may be electrically connected to the power source 104 and configured to receive current from and return current to the power source 104.

The plurality of contacts 184 at the first end 180 of the power cord assembly 138 may be configured such that when the plurality of contacts 184 are not in complete or sufficient electrical connection with the active contact 173 and the return contact 178, the power source 104 may generate and output the alarm or indication. Alternatively, when the plurality of contacts are in complete or sufficient electrical connection with the active and return contacts 173, 178, the power source 104 may deactivate the alarm or indication (assuming a sufficient or complete electrical connection exists between the active and return ports 140, 142 and the other parts of the active and return paths of the bipolar sphincterotome 102). In a particular example embodiment, the plurality of contacts 184 may include an active contact 184a, a first return contact 184b, and a second return contact 184c, which may be configured such that the alarm feature of the power source 104 may be utilized with the handle assembly 122.

Each of the contacts 184a, 184b, 184c may be electrically coupled to the active connector 186 or the return connector 188 via the active and return wires 144, 146a, 146b. In a particular configuration, the active contact 184a may be electrically connected to a first end 190 of the active wire 144. The active wire 144 may extend to a second end 192, which may be electrically connected to a conductive lead 193 of the active connector 186. In addition, the first return contact 184b may be electrically connected to a first end 194a of the first return wire 146a, and the second return contact 184c may be electrically connected to a first end 194b of the second return wire 146b. The first return wire 146a may extend from the first end 194a to a second end 196a, which may be electrically connected to a first return terminal 198a of the return connector 188. The second return wire 146b may extend from the first end 194b to a second end 196b, which may be electrically connected to a second return terminal 198b of the return connector 184. The first and second return terminals 198a, 198b may be adapted for removable connection with a pair of pin or leads of the return port 142.

In addition, each of the contacts 184a, 184b, 184c may be configured to be sufficiently electrically isolated from each other, at least when electrically disconnected from the active and return contacts 173, 178 of the handle assembly 122. Here, sufficient electrical isolation between the contacts 184a-c may include the active contact 184a being electrically isolated from the return contacts 184b, 184c such that interference between the active and return paths at the contacts 184a-c is sufficiently minimized. In addition, sufficient electrical isolation between the contacts 184a-c may include the return contacts 184b and 184c being completely isolated from each other or at least having a sufficiently high impedance between them when disconnected from the return contact 178 such that when the return connector 188 is connected to the return port 142 of the power source 104, the power source 104 detects a sufficiently high impedance between the return terminals 198a, 198b of the return connector 188, and in turn outputs an alarm or indication to indicate an insufficient or incomplete connection between the power source 104 and the bipolar sphincterotome 102.

That is, sufficient electrical isolation between the first return contact 184b and the second return contact 184c may yield a sufficiently high impedance between the first return terminal 198a and the second return terminal 198b, which may be detected by the power source 104, and in turn may cause the power source 104 to output the alarm or indication.

In some example configurations, as shown in FIG. 5, each of the contacts 184a, 186b, 186c may be disposed on a mating connector 200 that may be configured to mate or connect with a corresponding mating area 202 of the second gripping portion 128 that contains the active and return contacts 173, 178. The mating connector 200 of the power cord assembly 138 may be made of an insulating material, such as polycarbonate or plastic as examples. The contacts 184a, 184b, 184c may be sufficiently spaced apart from each other on the mating connector 200 to be sufficiently electrically isolated from each other.

Additionally, the contacts 184a, 184b, 184c may be sized, shaped, and/or positioned on the mating connector 200 to correspond to the size, shape, and/or positioning of the active and return contacts 173, 178 on the mating area 202. In general, the size, shape, and/or positioning of the contacts 184a, 184b, 184c on the mating connector 200 may correspond with the size, shape, and positioning of the active and return contacts 173, 178 such that when the mating connector 200 is mated with the mating area 202, the active contact 173 of the handle assembly 122 is in sufficient contact to form an electrical connection with the active contact 184a, and the return contact 178 of the handle assembly 122 is in sufficient contact to form an electrical connection with both the first return contact 184b and the second return contact 184c such that the first and second return contacts 184b, 184c are shorted together. When the first and second return contacts 184b, 184c are shorted together, the return contacts 184b, 184c may be insufficiently electrically isolated from each other, which may yield an insufficiently high impedance between the first and second return terminals 198a, 198b, and which in turn may cause the power source to deactivate or otherwise not output the alarm or indication. Alternatively, when the mating connector 200 of the power cord assembly 138 is separated from the corresponding mating area 202 and/or when the return contact 173 is in insufficient or incomplete contact with both the first and second return contacts 184b, 184c, the first and second return contacts 184b, 184c may be sufficiently electrically isolated from each other, which may cause the power source 104 to output the alarm or indication.

In the particular example embodiment shown in FIG. 5, the active and return contacts 173, 178 of the handle assembly 122 may be circular or disc-shaped or have circular or disc-shaped profiles. Correspondingly, the active contact 184a of the power cord assembly 122 may also be circular or disc-shaped and have the same or substantially the same size or diameter as the size or diameter of the active contact 173. In addition, the first and second return contacts 184b, 184c may be semicircular or have semicircular profiles and positioned relative to each other to form a circular profile. Other shapes, such as rectangular, triangular, polygonal, elliptical, or combinations thereof, may alternatively be used for the contacts 173, 178, 184a-c.

In addition, for some example configurations, the mating connector 200 and the mating area 202 may be removably attachable with each other. That is, the mating connector 200 may attach to and be detached from the corresponding mating area 202 of the handle assembly 122. A removably attachable connection between the mating connector 202 and the mating area 200 may be useful, particularly for bipolar sphincterotomes of limited usage, such as single-use bipolar sphincterotomes. After the bipolar sphincterotome has reached its usability limit, the power cord assembly 138 may be detached from the handle assembly 122 and used with a different bipolar sphincterotome. More generally and regardless of use, different bipolar sphincterotomes and power cord assemblies may be mixed and matched with each other through a removably attachable connection.

In turn, configuring the power cord assembly 138 in such a way as to cause the power source 104 to output an alarm in the event of a disconnection or an improper connection between the handle assembly 122 and the power cord assembly 138 may be a useful feature for bipolar sphincterotomes having a removably attachable connection. For example, a user may forget to connect the power cord assembly 138 to the handle assembly 122, or may improperly or connect the handle assembly 122 with the power cord assembly 138 such that there is an insufficient electrical connection between the active and/or return paths of the two assemblies 122, 138. By configuring the power cord assembly 122 to have dual return contacts 184*b*, 184*c* in order to utilize the alarm feature of the power source 104, a disconnection or an improper connection between the power cord assembly 138 and the handle assembly 122 may be quickly identified during use of the bipolar sphincterotome 102.

For some of these configurations, the removably attachable connection may be formed through magnetic coupling of the contacts. In particular, the contacts 173, 178, 184*a*, 184*b*, 184*c* may be magnetic elements. The active contact 173 may be magnetically attracted to the active contact 184*a*, and the return contact 178 may be magnetically attracted to each of the return contacts 184*b* and 184*c*. In other example configurations, non-magnetic coupling, rather than magnetic coupling, may be used to create the removably attachable connection. In still other alternative example configurations, the active and return portions of the power cord assembly 138 may be fixedly attached to the active and return portions of the handle assembly 122.

In addition, the active and return contacts 173, 178 may have different sizes or diameters. Where the contacts 173, 178, 184*a*-*c* are magnetic elements, configuring the contacts 173, 178 to have different sizes may enhance the magnetic coupling between the magnetic contacts. For example, as shown in FIG. 5, the active contact 173 may have a larger size or diameter than the return contact 178. Alternatively, the size differences may be reversed, with the active contact 173 having a smaller size or diameter than the return contact 178. In still other alternative configurations, the sizes between the active and return contacts 173, 178 may be substantially the same. As shown in FIG. 5, the sizes of the contacts 184*a*-*c* of the power cord assembly may correspond to the sizes of the active and return contacts 173, 178.

The above description describes a configuration of the mating connector 200 and the mating area 202 where, when the mating connector 200 is mated with the mating area 202, the active contact 173 of the handle assembly 122 contacts the active contact 184*a* of the power cord assembly 138, and the return contact 178 of the handle assembly 122 contacts and shorts together the return contacts 184*b*, 184*c* of the power cord assembly 138. Alternatively, the mating connector 200 and the mating area 202 may be oppositely configured such that when the mating connector 200 mates with the mating area 202, the return electrode 178 contacts the active contact 184*a*, and the active contact 173 contacts and shorts together the return electrodes 184*b*, 184*c*. In general, the mating connector 200 and the mating area 202 may be configured such that when they are mated together, one of the active contact 173 or the return contact 178 may contact the active contact 184*a*, and the other of the active contact 173 or the return contact 178 may contact and short together the return contacts 184*b*, 184*c* for electrical current to be transmitted from the power source 104 to the bipolar sphincterotome 102.

As previously described, the second gripping portion 128 may be fixedly attached with the handle stem portion 126, such that the first gripping portion 124 moves between the proximal and distal positions relative to both the handle stem portion 126 and the second gripping portion 128. Additionally, when the power cord assembly 138 is connected to the handle assembly 122 at the second gripping portion 128, the first gripping portion 124 may also move relative to the power cord assembly 138 rather than with the power cord assembly 138. In this way, the power cord assembly 138 may be considered to be relatively isolated from the movement of the first gripping member 124 as the first gripping portion 124 moves the cutting edge 118 between the relaxed and cutting positions, which may enhance operability of the bipolar sphincterotome 102.

Various embodiments may include all or some of the components described above. For example, a medical system may include the components shown in FIGS. 1A and 1B, including the bipolar sphincterotome 102 having the tubular member 106 and the handle assembly 122, the power source 104, and the power cord assembly 138. Other embodiments may include only the bipolar sphincterotome 102 with the handle assembly 122, which may be disconnected from the power cord assembly 138. Still other embodiments may include only the handle assembly 122, only the power cord assembly 138, or the power cord assembly 138 connected to handle assemblies for bipolar sphincterotomes other than the handle assembly 122. Other alternative embodiments may include the handle assembly 122 electrically connected to the power source 104 using a power cord assembly other than the power cord assembly 138, such as one that does not use a dual-active contact feature for alarm deactivation. Various combinations may be possible.

Figure 6:
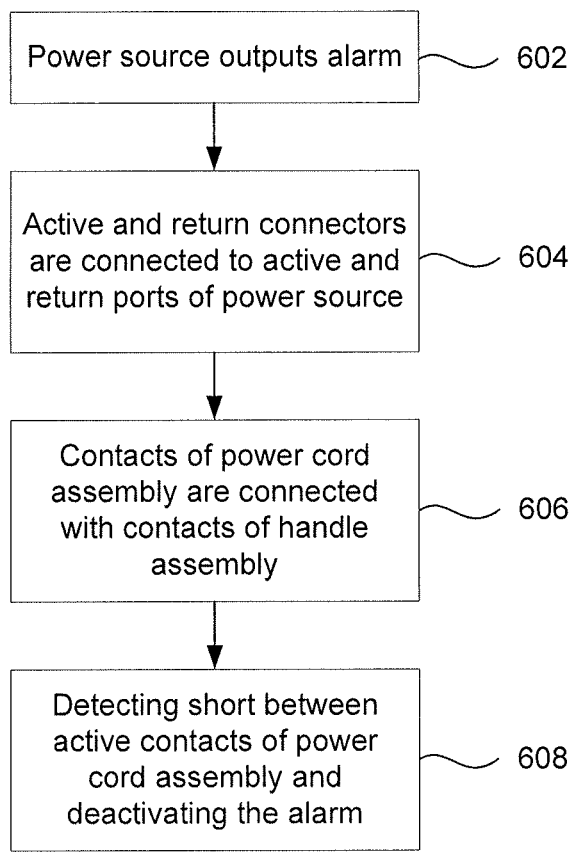
FIG. 6 shows a flow chart of a method of deactivating an alarm using a power cord assembly of a bipolar sphincterotome.

FIG. 6 shows a flow chart of an example method 600 of deactivating an alarm output by a power source when electrically connecting a bipolar sphincterotome to the power source. At block 602, the power source may output the alarm. The alarm be may any type of output, such as an audio or a visual output, that provides an indication to a user that the bipolar sphincterotome is not sufficiently electrically connected to the power source. At block 604, an active connector of a power cord assembly for the bipolar sphincterotome may be connected to an active port of the power source. Additionally, a return connector of the power cord assembly may be connected to a return port of the power source. At block 606, an active contact of the power cord assembly may be connected to either an active contact or a return contact on the handle assembly. Additionally, at block 606, a pair of return contacts of the power cord assembly may be connected to the other of the active contact or the return contact on the handle assembly, which may short together the pair of return contacts of the power cord assembly. In some example methods, the contacts of the power cord assembly may be connected to the contacts of the handle assembly through a removable connection or attachment, such as through magnetic coupling, of corresponding mating components of the power cord and handle assemblies. At block 608, the power source may detect the pair of return contacts of the power cord assembly shorted together. In response, the power source may deactivate the alarm.

The above description with respect to the drawings describes example embodiments of a handle assembly and a power cord assembly for bipolar sphincterotomes. In addition or alternatively, one or more both of the handle assembly or the power cord assembly, and/or features of the handle assembly and/or the power cord assembly, may be used for bipolar electrosurgical devices other than bipolar sphincterotomes. For example, the handle assembly 122 may be operably coupled to an active wire or other active component of any electrosurgical device that longitudinally moves the active component to perform the electrosurgical procedure. An example bipolar electrosurgical device other than the bipolar sphincterotome may be a bipolar endoscopic needle knife, which may distally advance and proximally retract an active cutting wire to perform the electrosurgical procedure.

As another example, the mating area 202 may be included on various handle assemblies for electrosurgical devices that generally include an active path and return path configured in a bipolar manner with an elongate tubular member that supply and return current to and from a treatment site to perform an electrosurgical procedure. The handle assembly may be of any configuration that enables a user to maneuver the electrosurgical device for performance of the electrosurgical procedure. The power cord assembly 138, including the mating connector 200, may be used with these bipolar electrosurgical devices. In addition, in the same way that the power cord assembly 138 may be used with different bipolar sphincterotomes as previously described, the power cord assembly 138 may be used interchangeably with different electrosurgical devices of different types. To illustrate, the power cord assembly 138 may be used with a bipolar sphincterotome and a bipolar needle knife, each having the mating area 202 integrated with their respective handle assemblies. Various adaptations and/or uses for the handle and power cord assemblies with electrosurgical devices may be possible.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A handle assembly for a bipolar electrosurgical device, the handle assembly comprising:
   an elongate handle stem portion comprising a body and a channel longitudinally extending in the body;
   a return portion of a return path of the bipolar electrosurgical device, the return portion comprising a return member disposed in the handle stem portion;
   a gripping portion movably disposed about the handle stem portion; and
   an active portion of an active path of the bipolar electrosurgical device, the active portion comprising an active member electrically connected to an active wire of the active path,
   wherein the gripping portion is configured to move the active wire in the channel relative to the return member and relative to the active member while the active member maintains being electrically connected with the active wire.

2. The handle assembly of claim 1, wherein the active member comprises a second active member, and wherein the active portion further comprises:
   a first active member longitudinally extending in the channel,
   wherein the first active member extends in the channel and contacts the second active member to form an electrical connection with the second active member and the active wire.

3. The handle assembly of claim 2, wherein the first active member is configured to slide across an outer surface of the second active member while maintaining electrical contact with the second active member as the gripping portion is moved about the handle stem portion.

4. The handle assembly of claim 2, wherein the first active member has a rounded end that contacts the outer surface of the second active member.

5. The handle assembly of claim 2, wherein the second active member is configured to flex when biased by the first active member as the gripping portion moves from a distal position to a proximal position.

6. The handle assembly of claim 2, wherein the second active member comprises:
   a distal portion disposed on a bottom inner surface of the handle stem portion; and
   a proximal portion that proximally extends upwardly from the bottom inner surface to a position along a proximal side inner surface of the handle stem portion,
   wherein the proximal portion of the second active member is configured to flex when biased by the first active member.

7. The handle assembly of claim 2, wherein the active portion further comprises a proximal active portion that electrically connects the second active member with a first active contact disposed on the handle assembly, and
   wherein the return portion further comprises a proximal return portion that electrically connects the return member with a first return contact disposed on the handle assembly.

8. The handle assembly of claim 2, wherein the first second active member comprises a conductive strip.

9. The handle assembly of claim 2, wherein the second active member is made of one of: Nitinol, spring steel, copper, or gold.

10. A bipolar electrosurgical device comprising:
    an elongate tubular member;
    an active path configured to deliver electrical current generated by a power source to a treatment site, the active path comprising an active wire movably disposed and longitudinally extending in the tubular member;
    a return path configured to return the electrical current to the power source; and
    a handle assembly comprising:
       an elongate handle stem portion comprising a body and a channel longitudinally extending in the body; and a gripping portion movably disposed about the handle stem portion and operably coupled to a proximal end of the active wire, wherein the return path comprises a return member disposed in the handle stem portion, wherein the active path further comprises an active member integrated with the handle assembly and electrically connected with the active wire, and wherein the gripping portion is configured to move the active wire in the channel relative to the return member and relative to the active member while the active member maintains being electrically connected with the active wire.

11. The bipolar electrosurgical device of claim 10, wherein the active member comprises a second active member, wherein the active path further comprises a first active member integrated with the handle assembly, wherein the first active member is fixedly attached to the gripping portion connected to the proximal end of the active wire; and wherein the second active member longitudinally extends in the channel, and wherein the first active member extends into the channel and contacts the second active member to form an electrical connection between the active wire, the first active member, and the second active member.

12. The bipolar electrosurgical device of claim 11, wherein the first active member is configured to slide across an outer surface of the second active member while maintaining electrical contact with the second active member as the gripping portion is moved about the handle stem portion.

13. The bipolar electrosurgical device of claim 11, wherein the first active member has a rounded end that contacts the second active member.

14. The bipolar electrosurgical device of claim 11, wherein the second active member is configured to flex when biased by the first active member as the gripping portion moves from a distal position to a proximal position.

15. The bipolar electrosurgical device of claim 14, wherein the second active member comprises:

a distal portion disposed on a bottom inner surface of the handle stem portion; and a proximal portion that proximally extends upwardly from the bottom inner surface to a position along a proximal side inner surface of the handle stem portion, where the proximal portion is electrically connected to a proximal conductive path of the handle assembly, wherein the proximal portion of the second active member is configured to flex when biased by the first active member.

16. The bipolar electrosurgical device of claim 11, wherein the second active member is made of one of: Nitinol, spring steel, copper, or gold.

17. The bipolar electrosurgical device of claim 11, wherein the second active member comprises a conductive strip.

18. The bipolar electrosurgical device of claim 11, wherein the active path further comprises a proximal active path portion that electrically connects the second active member with a first active contact disposed on the handle assembly, and wherein the return member further comprises a proximal return path portion that electrically connects the return member with a first return contact disposed on the handle assembly.

19. The bipolar electrosurgical device of claim 18, further comprising:

a power cord assembly configured for removable attachment with the handle assembly, wherein the power cord assembly comprises a plurality of contacts configured for electrical contact with the first active contact and the first return contact of the handle assembly, the plurality of contacts comprising:

a second active contact configured for electrical contact with the first active contact of the handle assembly; and a second return contact and a third return contact configured for electrical contact with the first return contact of the handle assembly.

20. The bipolar electrosurgical device of claim 19, wherein the second active contact, the second return contact, and the third return contact of the power cord assembly are disposed and sufficiently electrically isolated from each other on a mating connector, the mating connector configured to mate with a corresponding mating area of the handle assembly on which the first active contact and first return contact are disposed.

21. The bipolar electrosurgical device of claim 20, wherein the second return contact and the third return contact of the power cord assembly are electrically shorted together by the first return contact of the handle assembly when the mating connector is mated with the mating area of the handle assembly.

22. The bipolar electrosurgical device of claim 10, wherein the return member is disposed and longitudinally extending in the body of the handle stem portion.

* * * * *